United States Patent
Sakaki

(10) Patent No.: US 9,289,526 B2
(45) Date of Patent: Mar. 22, 2016

(54) ULTRASONIC DECONTAMINATION DEVICE

(71) Applicant: PHARMABIO CORPORATION, Aichi (JP)

(72) Inventor: Akio Sakaki, Aichi (JP)

(*) Notice: Subject to any disclaimer, the term of this patent is extended or adjusted under 35 U.S.C. 154(b) by 41 days.

(21) Appl. No.: 14/152,482

(22) Filed: Jan. 10, 2014

(65) Prior Publication Data

US 2014/0205499 A1    Jul. 24, 2014

(30) Foreign Application Priority Data

Jan. 22, 2013   (JP) .................. 2013-009063

(51) Int. Cl.
 *A61L 2/22*  (2006.01)
 *A61L 2/18*  (2006.01)
 *B05B 17/06* (2006.01)

(52) U.S. Cl.
 CPC . *A61L 2/22* (2013.01); *A61L 2/186* (2013.01); *A61L 2202/14* (2013.01); *B05B 17/0615* (2013.01); *B05B 17/0661* (2013.01); *B05B 17/0669* (2013.01)

(58) Field of Classification Search
 CPC .................. A61L 2/18; A61L 2/22
 USPC ..................................... 422/28
 See application file for complete search history.

(56) References Cited

U.S. PATENT DOCUMENTS

| | | | | |
|---|---|---|---|---|
| 2004/0256330 | A1* | 12/2004 | Okazaki | 210/756 |
| 2006/0140817 | A1 | 6/2006 | Cumberland et al. | |
| 2012/0083030 | A1* | 4/2012 | Busujima et al. | 435/303.1 |

FOREIGN PATENT DOCUMENTS

| | | |
|---|---|---|
| JP | 2010-154793 | 7/2010 |
| JP | 2011-036771 | 2/2011 |
| JP | 2011036771 A * | 2/2011 |
| WO | 02/064174 | 8/2002 |
| WO | 2011/047127 | 4/2011 |
| WO | 2011/099935 | 8/2011 |
| WO | WO 2011099935 A1 * | 8/2011 |
| WO | 2012/033850 | 3/2012 |
| WO | WO 2012033850 A2 * | 3/2012 |

OTHER PUBLICATIONS

English translation of Document No. JP 2011-036771 provided by Japan Patent Platform (www.j-platpat.inpit.go.jp); Feb. 2011.*
Search report from E.P.O., mail date is Aug. 13, 2014.

* cited by examiner

*Primary Examiner* — Kevin Joyner
*Assistant Examiner* — Holly Mull

(57) ABSTRACT

[Problem to be Solved] A device and a method for efficiently decontaminating a device used to culture cells are provided. [Means for Solving Problem] A decontamination device for decontaminating a device used to culture cells, manipulate microorganisms, or perform a sterility test, the device comprising an ultrasonic atomizer that atomizes a peracetic acid disinfectant by using ultrasonic oscillation to discharge droplets, a diffusion fan, a temperature-humidity sensor, and a controller.

10 Claims, 5 Drawing Sheets

○;DROPLETS

FIG. 3

| | PROCEDURE |
|---|---|
| (a) | SET REFERENCE TEMPERATURE ($T_1$) AND REFERENCE HUMIDITY ($H_1$) AND MEASURE EFFECTIVE DECONTAMINATION PERIOD ($t_1$) AT SET DECONTAMINATION HUMIDITY (H) MULTIPLE TIMES TO DETERMINE EFFECTIVE DECONTAMINATION PERIOD ($t_1$) |
| (b) | DETERMINE AMOUNT OF CHEMICAL TO BE SPRAYED BASED ON AMOUNT OF SATURATED WATER VAPOR $a(T_1)$ AT REFERENCE TEMPERATURE ($T_1$) AND RATIO BETWEEN REFERENCE HUMIDITY ($H_1$) AND MAXIMUM ACHIEVABLE HUMIDITY |
| (c) | DETERMINE AMOUNT OF CHEMICAL TO BE SPRAYED BASED ON AMOUNT OF SATURATED WATER VAPOR $a(T_0)$ AT INITIAL TEMPERATURE ($T_0$) AND RATIO BETWEEN INITIAL HUMIDITY ($H_0$) AND MAXIMUM ACHIEVABLE HUMIDITY |
| (d) | DETERMINE RATIO BETWEEN AMOUNT OF CHEMICAL AT REFERENCE TEMPERATURE/HUMIDITY AND AMOUNT OF CHEMICAL AT INITIAL TEMPERATURE/HUMIDITY BASED ON RATIOS IN (b) AND (c) |
| (e) | ADD CHEMICAL UNTIL INITIAL TEMPERATURE/HUMIDITY IN (c) CHANGES TO SET DECONTAMINATION HUMIDITY (H) AND MEASURE EFFECTIVE DECONTAMINATION PERIOD MULTIPLE TIMES TO DETERMINE EFFECTIVE DECONTAMINATION PERIOD |
| (f) | MULTIPLY EFFECTIVE DECONTAMINATION PERIOD ($t_1$) IN (a) BY RATIO OF CHEMICAL IN (d) |
| (g) | CONSIDER WEIGHTS FOR TEMPERATURE AND HUMIDITY IN SUCH A WAY THAT (f) IS APPROXIMATELY EQUAL TO (e) TO DETERMINE TEMPERATURE COEFFICIENT ($\alpha$) AND HUMIDITY COEFFICIENT ($\beta$), AND MULTIPLY TEMPERATURE AND HUMIDITY BY COEFFICIENTS |
| (h) | ADD PERIOD ($t_2$) FOR COMPENSATING ERROR OF HUMIDITY SENSOR TO (g) |
| (i) | ARBITRARY DECONTAMINATION PERIOD ($t_d$) CAN BE DETERMINED FROM THE FOLLOWING EXPRESSION BY INPUTTING INITIAL TEMPERATURE ($T_0$) AND INITIAL HUMIDITY ($H_0$): $t_d = \alpha \times a(T_1)/a(T_0) \times \beta \times H_1/(H-H_0) \times t_1 + t_2$ |

| | |
|---|---|
| DECONTAMINATION PERIOD | $t_d$ |
| EFFECTIVE DECONTAMINATION PERIOD AT REFERENCE TEMPERATURE AND HUMIDITY | $t_1$ |
| PERIOD FOR COMPENSATING ERROR OF TEMPERATURE-HUMIDITY SENSOR | $t_2$ |
| INITIAL TEMPERATURE IN DEVICE TO BE DECONTAMINATED | $T_0$ |
| INITIAL HUMIDITY IN DEVICE TO BE DECONTAMINATED | $H_0$ |
| REFERENCE TEMPERATURE | $T_1$ |
| REFERENCE HUMIDITY | $H_1$ |
| SET DECONTAMINATION HUMIDITY | H |
| AMOUNT OF SATURATE WATER VAPOR AT INITIAL TEMPERATURE | $a(T_0)$ |
| AMOUNT OF SATURATE WATER VAPOR AT REFERENCE TEMPERATURE | $a(T_1)$ |
| TEMPERATURE COEFFICIENT | $\alpha$ |
| HUMIDITY COEFFICIENT | $\beta$ |

ULTRASONIC DECONTAMINATION DEVICE

TECHNICAL FIELD

The present invention relates to a device and a method for decontaminating a device for culturing cells, manipulating microorganisms, or performing a sterility test; more specifically, to a device for atomizing an peracetic acid disinfectant by using an ultrasonic wave to decontaminate a device used to culture cells, manipulate microorganisms, or perform a sterility test and a method for decontaminating the device.

The present application asserts a priority claim for Japanese Patent Application 2013-009063, filed on Jan. 22, 2013, and the entire content thereof is incorporated by reference in the present specification.

BACKGROUND ART

At present, experiments and treatments using cells are diversified and performed in a variety of institutions and organizations for a variety of purposes. For example, these experiments and treatments include (1) basic studies primarily using animal cells and performed in university, state, and private research institutions, (2) basic studies using human cells and performed in medical college hospitals, state medical institutions, and pharmaceutical companies, (3) cell preparation for treatment purposes performed in medical college hospitals, pharmaceutical companies, and cell processing centers (CPCs) for medical treatment for which the patient bears the expense, (4) in microorganism operation, basic studies on pathogenic microorganisms that infect humans in university infection research laboratories and state infection research institutes, and (5) sterility tests performed in private food manufacturer examination section, agricultural laboratories, and hygienic laboratories.

Any of the studies using cells essentially requires experiments in a sterile or clean space. Since cells are very sensitive to infection and contamination, devices that handle cells are required to be extremely clean. It is, however, difficult to keep the device from contamination in everyday use, and it is therefore important to frequently clean and sterilize the device. Cleaning and sterilization of the device, however, have primarily involved rubbing-alcohol-based manual wiping and have not changed for about 30 years.

The rubbing-alcohol-based manual wiping can be readily performed, but a large burden is placed on operators and possible secondary contamination occurs during operation. Further, since the performance of the operation greatly depends on the skill of an individual operator, part of a device may unintentionally not be wiped, and the degree of achieved decontamination cannot be measured. Moreover, some fungi are not killed with rubbing alcohol, and persistently using the same chemical produces resistant bacterium. Spore-forming bacteria are not killed with rubbing alcohol either.

Some $CO_2$ incubators have a built-in decontamination function, but such devices are used for dedicated purposes and hence cannot be used with other device having no decontamination capability. Further, a device having a built-in decontamination function performs sterilization at about 120 degrees by using dry heat sterilization typically in a sterilization period of about two hours and hence requires about ten hours for heat dissipation, resulting in inefficient sterilization. Moreover, since the device becomes very hot during sterilization, the heat affects a $CO_2$ incubator located close to the device, which undesirably means that the nearby incubator cannot be used during the sterilization.

On the other hand, there is a known method in which a dedicated ultrasonic atomizer is placed in a $CO_2$ incubator and hydrogen peroxide vapor is produced for decontamination (Patent Reference 1). In this method, however, the interior of the incubator is considerably wet, which requires a wiping operation, possibly causing secondary contamination.

Further, a UV bactericidal lamp is used to decontaminate a clean bench and other safety cabinets. In this method, however, only an area directly irradiated with the UV light is sterilized. Further, when the UV light is reflected off walls or other surfaces, the sterilization effect is undesirably greatly reduced. Moreover, under the current circumstances, rubbing-alcohol-based manual wiping is performed on an area that is not irradiated with the UV light.

Further, in operation and experimentation using cell incubation and microorganisms, a centrifugal separator is frequently used, and a centrifugal separation step is a step having a high risk of generation of aerosol.

This is because a sprayed substance produced at the time of operation in a safety cabinet is likely to adhere to a centrifugal separating tube and centrifugal operation very strongly agitates the sprayed substance in the air in a centrifugal chamber.

Further, when an angle rotor is used, in particular, aerosol is generated in a gap between the centrifugal separating tube and a cap produced by a difference in distortion due to a centrifugal force.

The thus generated aerosol is known to have a high risk that causes cell contamination and operator infection.

However, decontamination of the interior of the chamber of a centrifugal separator has not been performed because there has been no acceptable decontamination method.

As described above, there has been no device that efficiently decontaminates the interior of a device used with cell incubation, such as a $CO_2$ incubator, a safety cabinet, and a centrifugal separator, without causing secondary contamination.

In studies in which infectious microorganisms are handled, the microorganisms are handled in a room designed to contain them for safety (P-3 room, P-4 room, and other biohazard rooms). In a safety cabinet in which unleashed microorganisms are handled, the microorganisms are likely to float therein or adhere thereto, but under the current circumstances, the cabinet is irradiated with UV light or rubbing-alcohol-based manual wiping is performed.

Further, to freeze and store the microorganisms, it is necessary to put them in a storage tube and take the storage tube out of the hazard room. In this process, an operator opens a door of the hazard room and places the tube in which the microorganisms have been placed in a pass box disposed in a space between the hazard room and a general area. The operator then opens a door of the general area and takes the tube out. In this process, it is typical that the tube is sealed and the outer surface thereof is cleaned with rubbing alcohol, but in the current state no checks are performed to determine that microorganisms are adhering to the outer surface of the tube in an exact sense.

As described above, there has been no device that prevents infection after aseptic operation and microorganism handling, specifically, that decontaminates not only the safety cabinet but also the biohazard room air in the pass box and the surface of the tube to be taken out.

Formalin gas fumigation is used for decontamination of the interior of a safety cabinet in some cases. Since formalin has, however, already been designated as a carcinogenic substance and is known to generate formic acid, paraformaldehyde, metaformaldehyde, and other highly corrosive, toxic residuals, formalin gas is hardly used under the current circumstances.

In food manufacturers and other places where sterility tests are frequently performed, microorganisms that adhere to food are inspected. To this end, culture-media-based incubation tests are typically performed. However, when a clean bench in which microorganisms are handled or a temperature controlled bath in which the incubation tests are performed is contaminated with fungi, accurate evaluation cannot be made. To avoid such a situation, rubbing-alcohol-based manual wiping is performed under the current circumstances.

As described above, there has been no device that readily decontaminates the interior of an inspection device from a quality control perspective either.

PRIOR ART REFERENCES

Patent References

Patent Reference 1: Japanese Patent Laid-Open No. 2010-154793

SUMMARY OF THE INVENTION

Problems to be Solved by the Invention

An object of the invention is to provide a device and a method for efficiently decontaminating a device used to culture cells, manipulate microorganisms, or perform a sterility test.

Means for Solving the Problems

In view of the problems with the related art as described above, the present inventors conducted intensive studies and found that atomizing a peracetic acid disinfectant by using an ultrasonic wave allows very-small-diameter droplets (dry fog) to be discharged and spraying the droplets in a device used to culture cells, manipulate microorganisms, or perform a sterility test (hereinafter also referred to as "device to be decontaminated") allows effective decontamination of the device to be decontaminated without any damage thereto due to corrosion because the droplets do not condense.

The present inventors have further found that calculating an accurate decontamination period based on the temperature and humidity in the device to be decontaminated to exactly control the humidity in the device allows efficient vaporization of the peracetic acid disinfectant and hence stable decontamination at a high level. The inventors accordingly arrived at the invention.

That is, the invention provides the following device and method:

[1] A device for decontaminating a device used to culture cells, manipulate microorganisms, or perform a sterility test, said decontamination device comprising:

an ultrasonic atomizer for atomizing a peracetic acid disinfectant by using ultrasonic oscillation to discharge droplets;
 a diffusion fan;
 a temperature-humidity sensor; and
 a controller.

[2] The decontamination device described in [1], wherein the peracetic acid disinfectant is a mixture of peracetic acid, hydrogen peroxide, acetic acid, and water.

[3] The decontamination device described in [1] or [2], wherein the controller has an automatic decontamination-period-calculating function.

[4] The decontamination device described in any one of [1] to [3], wherein the controller has an automatic decontamination-period-calculating function for calculating the decontamination period based only on the temperature and humidity in the device to be decontaminated.

[5] The decontamination device described in any one of [1] to [4], wherein the droplets discharged from the ultrasonic atomizer have a diameter measurable in microns.

[6] The decontamination device described in any one of [1] to [5], further comprising a catalyst fan.

[7] The decontamination device described in any one of [1] to [6], wherein the device used to culture cells, manipulate microorganisms, or perform a sterility test is a $CO_2$ incubator, a safety cabinet, a pass box, a clean bench, a temperature controlling device, or a centrifugal separator.

[8] The decontamination device described in any one of [1] to [7], wherein the ultrasonic atomizer is provided with at least one component selected from the following components: the temperature-humidity sensor, the diffusion fan, and the catalyst fan.

[9] A method for decontaminating a device used to culture cells, manipulate microorganisms, or perform a sterility test, the method comprising: placing an ultrasonic atomizer in the device used to culture cells, manipulate microorganisms, or perform a sterility test; activating the ultrasonic atomizer to atomize a peracetic acid disinfectant by using the resultant ultrasonic wave to discharge droplets; and causing the droplets to come into contact with the device.

[10] The method described in [9], wherein the peracetic acid disinfectant is atomized and discharged in the form of the droplets until the humidity in the device reaches a predetermined value, whereupon the ultrasonic atomizer is repeatedly activated and deactivated to maintain the predetermined humidity.

[11] The method described in [9] or [10], wherein the ultrasonic atomizer is repeatedly activated and deactivated to maintain the humidity in the device at the set humidity after the humidity is set before decontamination is initiated, and the peracetic acid disinfectant is atomized and discharged in the form of the droplets until the humidity in the device reaches the set value.

[12] The method described in [11], wherein before decontamination is initiated, a temperature-humidity sensor is used to measure the temperature and humidity in the device to calculate a decontamination period at the set humidity.

[13] The method described in any one of [9] to [12], wherein a diffusion fan is used to diffuse the droplets in the device.

Effects of the Invention

In the decontamination device and the decontamination method according to the invention, since atomizing a peracetic acid disinfectant by using ultrasonic waves allows very-small-diameter droplets to be discharged, a device to be decontaminated or any other device can be effectively decontaminated without any damage thereto due to corrosion. Further, since the droplets do not wet the interior of the device, no secondary contamination due to liquid wiping operation will occur.

Further, since peracetic acid has a wide antibacterial spectrum, using the device according to the invention allows spore-forming bacteria and other similar bacteria, which cannot be sterilized by using related art, can be effectively sterilized.

Moreover, since the decontamination device according to the invention has the automatic decontamination-period-calculating function, any operator can operate the decontamination device to provide a stable decontamination level without an excessive amount of sprayed disinfectant or non-decontaminated portions.

BRIEF DESCRIPTION OF THE DRAWINGS

FIG. 3 shows an example of an algorithm useable in the decontamination device and a decontamination method of the invention.

DESCRIPTION OF THE PREFERRED EMBODIMENTS

Figure 1:
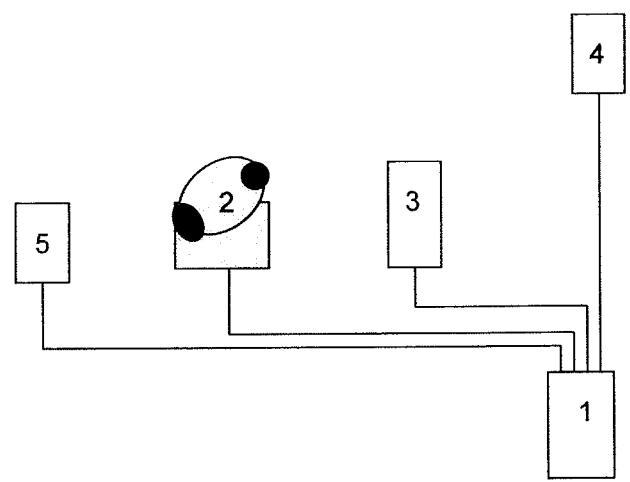
FIG. 1 is a schematic view of an embodiment of a decontamination device according to the invention.

An embodiment of the invention relates to a device for decontaminating a device used to culture cells, manipulate microorganisms, or perform a sterility test, and the decontamination device includes an ultrasonic atomizer that atomizes an peracetic acid disinfectant by using ultrasonic oscillation to discharge droplets, a diffusion fan, a temperature-humidity sensor, and a controller, and a catalyst fan in some cases (hereinafter also referred to as "decontamination device of the invention").

The ultrasonic atomizer used in the invention can cause an atomizing oscillator to oscillate and use the resultant ultrasonic waves to atomize a liquid.

The atomizing oscillator used in the ultrasonic atomizer preferably includes a piezoelectric element made of a piezoelectric ceramic; and an insulating resin film located in the piezoelectric element and coated on a deposition surface including a liquid facing surface that faces a liquid. The atomizing oscillator has a configuration in which the liquid facing surface faces the liquid and the insulating resin film is in contact with the liquid. The insulating resin film is preferably made of a paraxylene-based polymer having a thickness ranging from 5 to 20 μm and produced by depositing a monomer on the deposition surface of the piezoelectric element with the deposited layer and the monomer polymerized to each other for resinification.

Further, as the ultrasonic atomizer used in the invention, the piezoelectric element preferably has a plate-like shape and includes a piezoelectric ceramic plate having a first principal surface, a second principal surface, and a side surface that connects the first and second principal surfaces to each other; a first electrode layer that spreads over the first principal surface and extends via the side surface to the second principal surface; and a second electrode layer that is separated from the first electrode layer, spreads over the second principal surface, and faces the first electrode layer on the first principal surface via the piezoelectric ceramic plate. The piezoelectric element is also preferably configured so that the insulating resin film is coated on the deposition surface formed of the first principal surface, the side surface, and the first electrode layer formed on the first principal surface and the side surface, and that the first principal surface faces the liquid.

Further, the piezoelectric ceramic plate is preferably an atomizing oscillator sized to resonate in the thickness direction thereof when an electric signal oscillating at a frequency ranging from 1 to 5 MHz is applied between the first electrode layer and the second electrode layer.

The thus configured ultrasonic atomizer is described in detail in Japanese Patent Laid-Open No. 2011-36771, and the description in the patent reference is incorporated by reference within the scope of the invention.

The ultrasonic atomizer in the invention is connected to the controller and activated and deactivated under the control of the controller.

The ultrasonic atomizer in the invention is preferably designed so that when the amount of chemical decreases to a value below a necessary amount, the ultrasonic atomizer displays a low chemical level and suspends the atomizing operation and immediately stops counting down if the device is performing decontamination. Further, it is safer to design the ultrasonic atomizer in such a way that it is paused or does not start atomizing immediately after the chemical is replenished. After the atomizing operation and a set humidity is reached again, the ultrasonic atomizer starts counting down a decontamination period again.

The ultrasonic atomizer in the invention preferably has a function of logging the temperature and humidity and automatically records them, for example, at 1-minute intervals. The log records can be saved in a single file in the *.CSV format whenever a single run of decontamination is completed.

The peracetic acid disinfectant used in the invention is preferably formed of a mixture of peracetic acid, hydrogen peroxide, acetic acid, and water.

Preferable contents of each component of the peracetic acid disinfectant in the invention are as follows: the peracetic acid content ranges from 0.01 to 1.2% by weight; the hydrogen peroxide content ranges from 0.06 to 4.8% by weight; the acetic acid content ranges from 0.02 to 6.0% by weight; and the remainder is water.

Examples of the peracetic acid disinfectant useable in the invention include ACTRIL (registered trademark) and MINNCARE (registered trademark), both of which are commercially available from Minntech Corporation, and other peracetic-acid-based chemicals.

In the invention, in the ultrasonic atomizer described above, the atomizing oscillator is caused to oscillate, and the resultant ultrasonic waves are used to atomize the peracetic acid disinfectant. Droplets having a very small diameter (micron-sized droplets) can thus be produced. The median diameter of the droplets preferably ranges from 3 to 15 μm, more preferably 3 to 10 μm. Droplets having such a very small size are also called dry fog and behave like a fog having no wetting characteristic, whereby they can effectively decontaminate a device to be decontaminated without any damage due to corrosion. Further, since the droplets do not wet the interior of the device, secondary contamination that occurs in a liquid wiping process will not occur.

Further, since peracetic acid has a wide antibacterial spectrum, using the device according to the invention allows spore-forming bacteria, which cannot be sterilized in a short period by using a method of related art using hydrogen peroxide vapor, to be killed in a short period.

The decontamination device of the invention includes a diffusion fan. The diffusion fan has a fan motor and rotates when the motor rotates. The diffusion fan can be connected to the ultrasonic atomizer. The diffusion fan makes the distribution of disinfectant particles in the device to be decontaminated uniform. The diffusion fan is believed to further encourage the small particles not only to be evaporated but also to produce free radicals for enhancement of the decontamination effect.

The decontamination device of the invention can comprise a catalyst fan. The catalyst fan is connected to the controller for use when there is a need to decompose in a short period the hydrogen peroxide in the device to be decontaminated having undergone decontamination. The catalyst fan includes a fan motor and a catalyst, the fan rotating when the fan motor rotates, and allowing the outside air to efficiently pass through the catalyst to decompose the hydrogen peroxide.

The decontamination device of the invention includes a temperature-humidity sensor. The temperature-humidity sensor is connected to the controller and transmits detection values of measured temperature and humidity to the controller. The transmitted detection values can be displayed on the controller in real time and automatically recorded at 1-minute intervals. The records (log) are recorded in USB memory in the controller in the form of a *.CSV file, and the data can be transferred to an external computer for checking. The temperature-humidity sensor can be kept reliable by calibration. In the invention, the temperature-humidity sensor can be disposed in an appropriate position in the interior of the device to be decontaminated at the time of decontamination.

The decontamination device of the invention comprises a controller. The controller in the invention is electrically connected to the ultrasonic atomizer, the diffusion fan, the temperature-humidity sensor, and the catalyst fan. The controller initiates the action of the ultrasonic atomizer to cause the diffusion fan to start blowing air for decontamination. During the decontamination, the controller activates or deactivates the ultrasonic atomizer based on the detection values from the temperature-humidity sensor in such a way that the humidity in the device to be decontaminated detected with the temperature-humidity sensor is maintained at a preset humidity value. When the decontamination is completed, the catalyst fan is activated to decompose the hydrogen peroxide in the device to be decontaminated.

The controller of the invention is characterized by an automatic decontamination-period-calculating function. That is, before decontamination is initiated, the controller uses the temperature-humidity sensor to measure the temperature in the device to be decontaminated and calculates the amount of saturated vapor at the temperature. The controller then measures the humidity in the device to be decontaminated. Based on the measured humidity and the amount of saturated vapor determined above, the controller calculates the amount of water vapor in the device to be decontaminated. The controller can thus calculate an approximate amount of droplets of the peracetic acid disinfectant that can be sprayed into the device to be decontaminated. Further, based on the calculated amount of peracetic acid disinfectant to be sprayed, the controller can find out a decontamination period starting from the time when a predetermined humidity set in advance and to be maintained in the device to be decontaminated is reached and ending at the time when the decontamination is completed based on an algorithm created by referring to a large number of decontamination condition test results. FIG. 3 shows an example of the algorithm useable in the automatic decontamination-period-calculating function of the controller of the invention.

The decontamination device of the invention, which has the automatic decontamination-period-calculating function described above, does not need to spray an excessive amount of disinfectant and can calculate a decontamination period based only on the temperature and humidity in the device to be decontaminated, whereby any operator can operate the decontamination device to provide a stable decontamination level without non-decontaminated portions.

The controller in the invention can operate in the following modes: a manual mode in which the operator can manually input a humidity setting, a humidification period, and a catalyst fan operating period for decontamination; a memory mode in which three sets of the preset values can be recorded; and an automatic mode in which the operator only needs to place the temperature-humidity sensor and does not need to make the other settings for decontamination.

Figure 2:
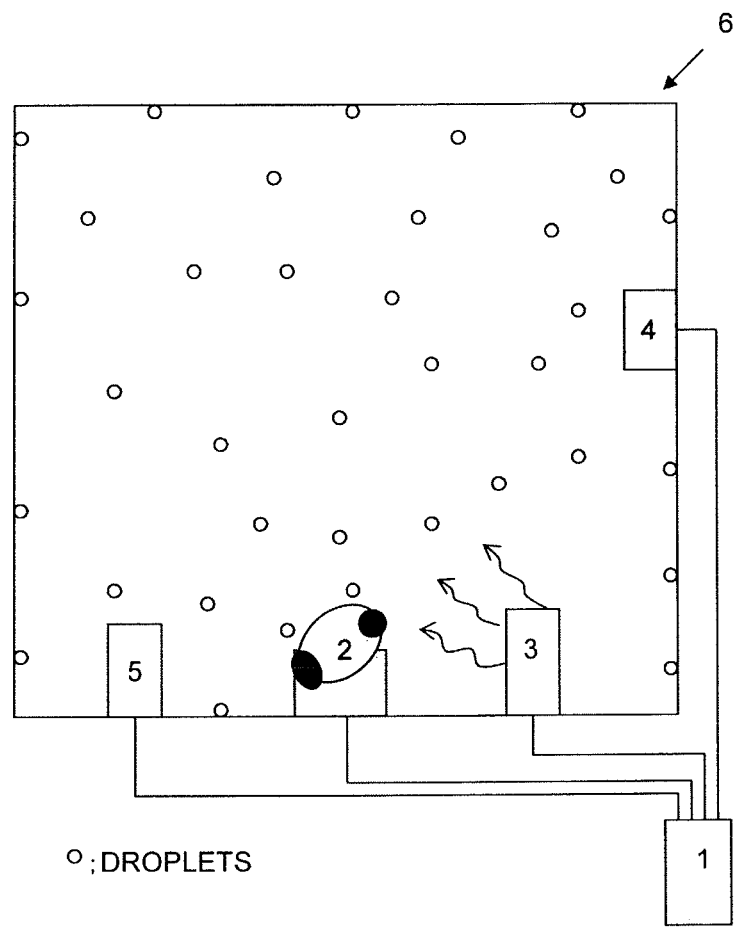
FIG. 2 is a schematic view showing that the decontamination device according to the invention is used to decontaminate a $CO_2$ incubator.

The decontamination device of the invention can be configured so that the ultrasonic atomizer, the temperature-humidity sensor, and the diffusion fan, and the catalyst fan in some cases are electrically connected to the controller. FIG. 1 is a schematic view of the decontamination device of the invention according to the thus configured embodiment. FIG. 2 is a schematic view showing that the decontamination device is used to decontaminate a $CO_2$ incubator. As shown in FIG. 2, the ultrasonic atomizer discharges droplets, and the diffusion fan diffuses the droplets across the interior of the $CO_2$ incubator.

The decontamination device of the invention can instead be configured so as to include the ultrasonic atomizer provided and be integrated with at least one component selected from the temperature-humidity sensor; the diffusion fan; and the catalyst fan, and the controller. In this case, the integrated unit and the controller can be electrically connected to each other. Alternatively, the controller can control the integrated unit via wireless communication.

Another embodiment of the invention relates to a method for decontaminating a device used to culture cells, manipulate microorganisms, or perform a sterility test, the method including placing an ultrasonic atomizer in the device used to culture cells, manipulate microorganisms, or perform a sterility test; activating the ultrasonic atomizer to atomize a peracetic acid disinfectant by using the resultant ultrasonic wave to discharge droplets; and causing the droplets to come into contact with the device.

In the decontamination method of the invention, the peracetic acid disinfectant is atomized and discharged in the form of the droplets until the humidity in the device to be decontaminated reaches a predetermined value, and then the ultrasonic atomizer can be repeatedly activated and deactivated to maintain the predetermined humidity.

Further, after the humidity is set before decontamination is initiated, the peracetic acid disinfectant is atomized and discharged in the form of the droplets until the humidity in the device to be decontaminated reaches the set value, and then the ultrasonic atomizer can be repeatedly activated and deactivated to maintain the humidity in the device at the set humidity.

Further, in the decontamination method of the invention, before decontamination is initiated, the temperature-humidity sensor can be used to measure the temperature and humidity in the device to be decontaminated to calculate a decontamination period at a set humidity. This is achieved by using the method described above to measure the temperature in the device to be decontaminated by using the temperature-humidity sensor before decontamination is initiated to calculate the amount of saturated vapor at the temperature; then measure the humidity in the device to be decontaminated to calculate the amount of peracetic acid disinfectant to be sprayed necessary to achieve the maximum humidity; and calculates a decontamination period stating from the time when a predetermined humidity set in advance and to be maintained in the device to be decontaminated is reached by using an algorithm created by referring to a large number of decontamination condition test results. FIG. 3 shows an example of the algorithm useable in the decontamination method of the invention.

Figure 4:
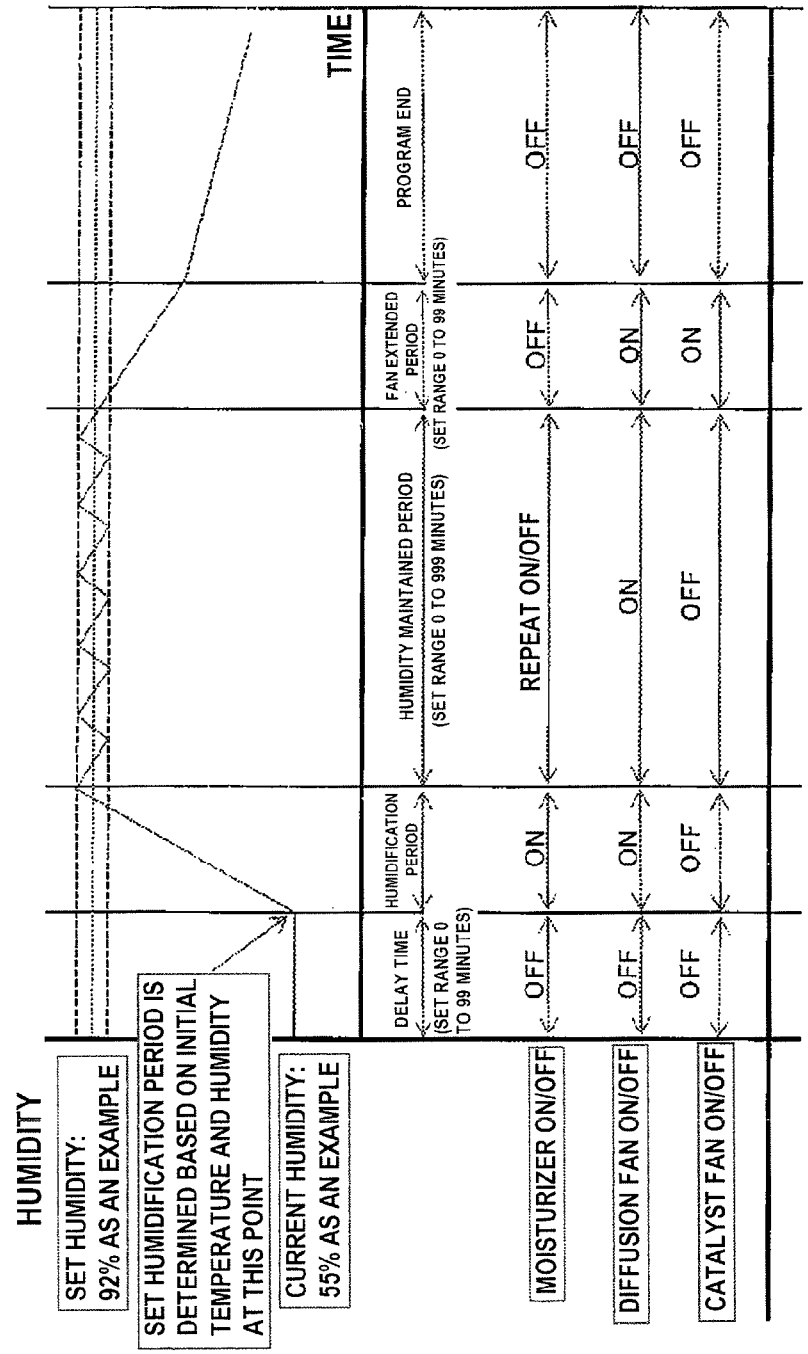
FIG. 4 shows an example of a decontamination process based on the decontamination method of the invention.

FIG. 4 shows an example of the decontamination process based on the decontamination method of the invention.

As shown in FIG. 4, during the moisturization period, a moisturizer (ultrasonic atomizer) and the diffusion fan are activated, whereas during the humidity maintaining period, the moisturizer is repeatedly so turned on and off that the set humidity is maintained in accordance with the humidity detected with the temperature-humidity sensor.

The decontamination device of the invention can be used with a device used to culture cells, manipulate microorganisms, or perform a sterility test, such as a $CO_2$ incubator, a safety cabinet, a pass box, a centrifugal separator chamber, a clean bench, and a temperature controlling device.

EXAMPLES

Example 1

*G. stearothermophilus* (ATCC #7953), which is a spore-forming bacterium (the number of which is $10^6$), was used as BI. A sterilization period was automatically calculated by using the automatic calculation function, and operation of killing the $10^6$ spore-forming bacteria in a variety of temperature and initial humidity environments was checked. The following table shows results of the checking.

TABLE 1

| Temperature | Normal humidity | High humidity (80% PH) |
|---|---|---|
| 15° C. | 80%, 273 minutes negative (−) | 273 minutes negative (−) |
| 25° C. | 39%, 84 minutes negative (−) | 162 minutes negative (−) |
| 35° C. | 23%, 61 minutes negative (−) | 124 minutes negative (−) |
| 45° C. | 10%, 49 minutes negative (−) | 103 minutes negative (−) |

Example 2

The decontamination device of the invention (ACTRIL was used as peracetic acid disinfectant) was used to perform sterility tests on a $CO_2$ incubator (manufactured by Ikemoto Scientific Technology Co., Ltd., model 10-0211) and a safety cabinet (manufactured by Sanyo Electric Co., Ltd., model MHW-132AJ). As a biological indicator (BI), *Aspergillus brasilus Niger* (NBRC 9455), which is prepared fungus spores (the number of which is $10^6$), and *G. stearothermophilus* (ATCC #7953), which is a spore-forming bacterium (the number of which is $10^6$), were used. Further, a sterilization period (humidity maintained period) was automatically calculated by using the automatic decontamination-period-calculating function. The following tables show results of the tests.

TABLE 2

Result of test on $CO_2$ incubator

| | B placement location and incubation result | | |
|---|---|---|---|
| BI | Upper level | Intermediate level | Lower level |
| Fungi $10^6$ | Negative (−) | Negative (−) | Negative (−) |
| Bacteria $10^6$ | Negative (−) | Negative (−) | Negative (−) |

Set humidity: 95%
Initial temperature 37° C., Initial humidity: 33%
Humidity maintained period: 63 minutes

TABLE 3

Test results for safety cabinet

| | B placement location and incubation result | | |
|---|---|---|---|
| BI | Left | Center | Right |
| Fungi $10^6$ | Negative (−) | Negative (−) | Negative (−) |
| Bacteria $10^6$ | Negative (−) | Negative (−) | Negative (−) |

Set humidity: 95%
Initial temperature: 23° C., Initial humidity: 64%
Humidity maintained period: 114 minutes Tables 2 and 3, which shows results of the sterility tests performed for the humidity maintaining period determined by the automatic calculation using the automatic decontamination-period-calculating function, show that the fungus spores and the spore-forming bacteria can be effectively sterilized.

Example 3

Effect of Catalyst Fan

Figure 5:
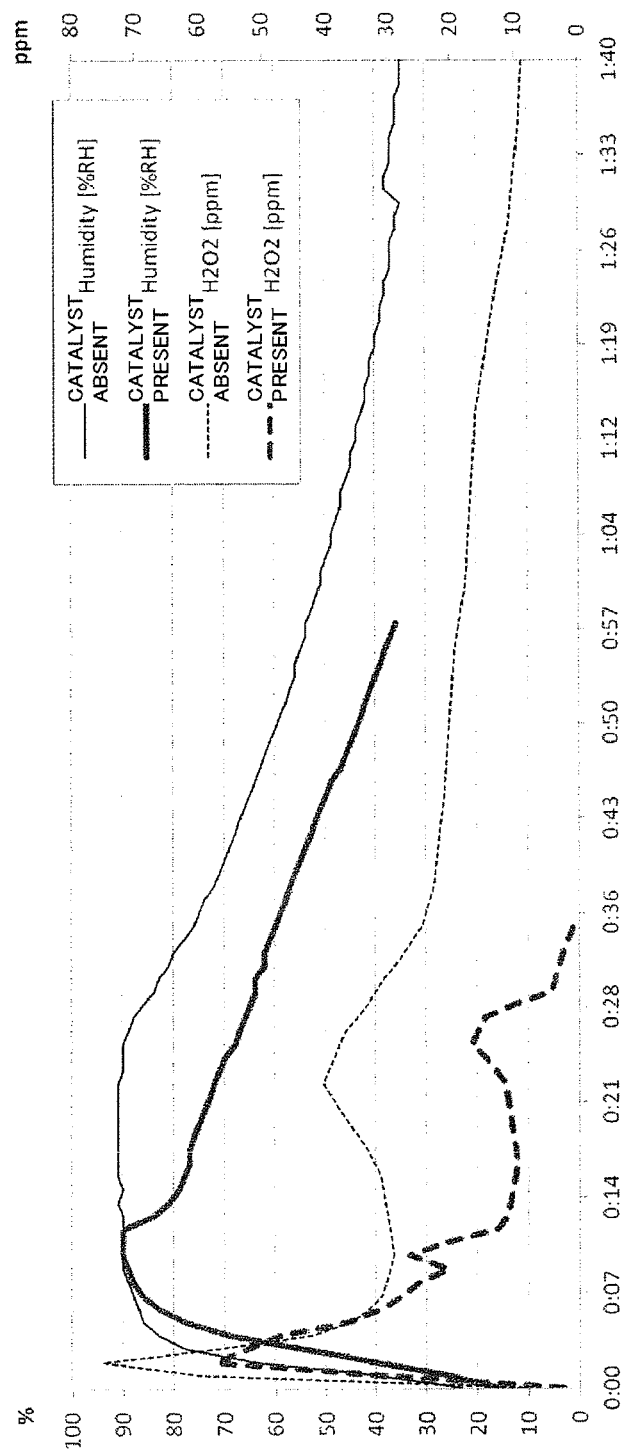
FIG. 5 shows results of measurement of the concentration of hydrogen peroxide in a case where a catalyst fan is used and a case where no catalyst fan is used.

In the decontamination device of the invention, to check an effect of the catalyst fan, the concentration of the hydrogen peroxide was measured in the following cases: (1) the catalyst fan is not used after the sterilization; and (2) the catalyst fan is used after the sterilization. FIG. 5 shows results of the measurement.

As apparent from FIG. 5, use of the catalyst fan allows the concentration of residual hydrogen peroxide after the sterilization to be quickly lowered.

EXPLANATION OF NUMERICAL AND CHARACTERS

1 Controller
2 Ultrasonic atomizer
3 Diffusion fan
4 Temperature-humidity sensor
5 Catalyst fan
6 $CO_2$ incubator

The invention claimed is:
1. A decontaminator for decontaminating a device having an interior space that is used to culture cells, manipulate microorganisms, or perform a sterility test, the decontaminator comprising:
an ultrasonic atomizer for atomizing a peracetic acid disinfectant by using ultrasonic oscillation to discharge droplets;
a diffusion fan;
a temperature-humidity sensor; and
a controller, wherein the ultrasonic atomizer and temperature-humidity sensor are configured to be placed within the interior space of the device that is to be decontaminated, wherein the controller has an automatic decontamination-period-calculating function that calculates a decontamination period time based only on the temperature and humidity in the device to be decontaminated, wherein the ultrasonic atomizer is configured to display a low chemical level, suspend the atomizing operation, and immediately stop counting down the decontamination period time if the device is performing decontamination when an amount of a chemical decreases to a value below necessary amount, wherein the ultrasonic atomizer is configured to pause a restart of the atomizing after the chemical is replenished above the necessary amount, and wherein after a set humidity is reached, the ultrasonic atomizer is configured to start counting down rest of the decontamination period time.

2. The decontaminator according to claim 1, wherein the peracetic acid disinfectant is a mixture of peracetic acid, hydrogen peroxide, acetic acid, and water.

3. The decontaminator according to claim 1, wherein the droplets discharged from the ultrasonic atomizer have a diameter measurable in microns.

4. The decontaminator according to claim 1, further comprising a catalyst fan.

5. The decontaminator according to claim 1, wherein the device to be contaminated is a $CO_2$ incubator, a safety cabinet, a pass box, a clean bench, a temperature controlling device, or a centrifugal separator.

6. The decontaminator according to claim 1, wherein the ultrasonic atomizer is provided with at least one component selected from the temperature-humidity sensor, the diffusion fan, and the catalyst fan.

7. The decontaminator according to claim 1, wherein the ultrasonic atomizer comprises:
a plate-shaped piezoelectric element and includes a piezoelectric ceramic plate having a first principal surface, a second principal surface, and a side surface that connects the first and second principal surfaces to each other;
a first electrode layer that spreads over the first principal surface and extends via the side surface to the second principal surface; and
a second electrode layer that is separated from the first electrode layer, spreads over the second principal surface, and faces the first electrode layer on the first principal surface via the piezoelectric ceramic plate.

8. A method for decontaminating a device having an interior space that is used to culture cells, manipulate microorganisms, or perform a sterility test, the method comprising:
placing an ultrasonic atomizer within the interior space of the device that is to be decontaminated;
measuring temperature and humidity in the device to be decontaminated;
calculating a decontamination period time based only on the temperature and humidity in the device to be decontaminated;
activating the ultrasonic atomizer to atomize a peracetic acid disinfectant by using the resultant ultrasonic wave to discharge droplets;
causing contact between the droplets and the device;
displaying a low chemical level, suspending the atomizing operation, and immediately stopping counting down the decontamination period time if the device is performing decontamination when an amount of a chemical decreases to a value below a necessary amount;
pausing a restart of the atomizing after the chemical is replenished above the necessary amount; and
after a set humidity is reached, starting counting down rest of the decontamination period time.

9. The method according to claim 8, wherein a diffusion fan is used to diffuse the droplets in the device.

10. The method according to claim 8, the ultrasonic atomizer comprises:
a plate-shaped piezoelectric element and includes a piezoelectric ceramic plate having a first principal surface, a second principal surface, and a side surface that connects the first and second principal surfaces to each other;
a first electrode layer that spreads over the first principal surface and extends via the side surface to the second principal surface; and
a second electrode layer that is separated from the first electrode layer, spreads over the second principal surface, and faces the first electrode layer on the first principal surface via the piezoelectric ceramic plate.

* * * * *